United States Patent [19]

Lu et al.

[11] Patent Number: 5,446,025
[45] Date of Patent: Aug. 29, 1995

[54] FORMULATIONS AND METHOD OF THE PERCUTANEOUS ADMINISTRATION OF LEUPROLIDE

[75] Inventors: Mou-Ying Fu Lu, Lake Bluff; Gowdahallin N. Subba Rao, Mundelein; Dennis Y. Lee, Highland Park, all of Ill.

[73] Assignee: Abbott Laboratories, Abbott Park, Ill.

[21] Appl. No.: 897,680

[22] Filed: Jun. 12, 1992

[51] Int. Cl.$^6$ .................. A61K 37/00; A61K 37/02; C07K 5/00; C07K 7/00
[52] U.S. Cl. ........................ 514/15; 530/313; 530/328
[58] Field of Search .................. 514/15; 530/313, 328

[56] References Cited

FOREIGN PATENT DOCUMENTS 2025078  3/1991  Canada .................. A61K 35/78

Primary Examiner—Robert J. Hill, Jr.
Assistant Examiner—A. M. Davenport
Attorney, Agent, or Firm—Jerry F. Janssen

[57] ABSTRACT

Compositions useful for the percutaneous administration of leuprolide comprise from about 1 to about 100 mg/ml of leuprolide in its free base form, a cutaneous membrane penetration enhancing component, and a pharmaceutically acceptable carrier. The cutaneous membrane transport enhancing component comprises from about 1 percent to about 15 percent urea, from 1 percent to about 5 percent menthol, from about 0.5 percent to about 5 percent methyl salicylate, and from about 0.5 percent to about 5 percent camphor, all percentages expressed in weight/volume based upon the total volume of the composition.

7 Claims, 1 Drawing Sheet

FORMULATIONS AND METHOD OF THE PERCUTANEOUS ADMINISTRATION OF LEUPROLIDE

TECHNICAL FIELD

The present invention relates to pharmaceutical formulations and a medical method of treatment. More particularly, the present invention concerns formulations containing leuprolide in the free base form and a method for the percutaneous administration of leuprolide in the free base form.

BACKGROUND OF THE INVENTION

The gonadotropins, follicle stimulating hormone (FSH), luteinizing hormone (LH), and chorionic gonaotropin (CG) are required for ovulation, spermatogenesis, and the biosynthesis of sex steroids. A single hypothalamic hormone, gonadotropin-releasing hormone (GnRH, also known as luteinizing hormone-releasing hormone, LHRH, Sequence ID. No. 1) is responsible for regulating the secretion of both FSH and LH in mammals.

In recent years considerable research effort has been expended on finding synthetic analogs of LHRH. These efforts have produced a number of LHRH agonists and antagonists. One such LHRH agonist is leuprolide (Sequence ID. No. 2), a nonapeptide having the structure:

which is disclosed and claimed in U.S. Pat. No. 4,005,063 to Gendrich, et al. Leuprolide is a potent LHRH agonist which, when introduced to the portal circulation, induces the release of luteinizing hormone (LH) and follicle stimulating hormone (FSH) from the anterior pituitary. The oral bioavailability of leuprolide is low, hence the drug is typically administered either subcutaneously in daily doses as the acetate salt or monthly by intramuscular injection of a prolonged-release depot formulation in which the acetate salt is encapsulated in microcapsule form.

Various non-parenteral routes of administration of leuprolide acetate have been tested with limited success including aerosol formulations, nasal spray formulations, and iontophoretic systems.

SUMMARY OF THE INVENTION

Figure 1:
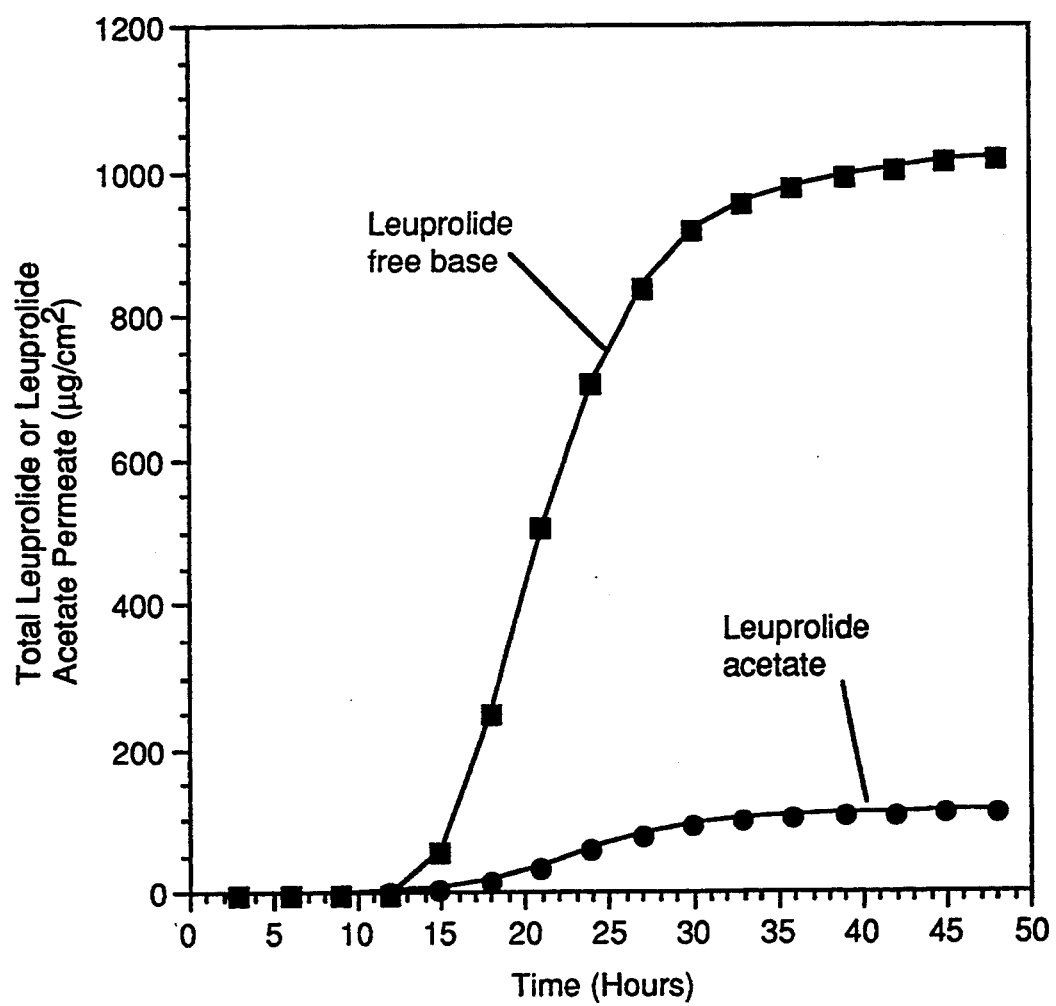
FIG. 1 is a graph illustrating the cumulative amount of leuprolide free base and leuprolide acetate permeated through human skin tissue over time in an in vitro test.

In accordance with the principal aspect of the present invention, it has been found that the bioavailability of non-parenterally administered leuprolide is considerably enhanced by introducing the free base form of leuprolide percutaneously in a formulation which comprises the leuprolide free base active therapeutic ingredient, a pharmaceutically acceptable carrier, and a cutaneous membrane penetration enhancing component comprising from about 3 percent to about 30 percent of the formulation. The cutaneous membrane penetration enhancing component comprises from about 1 percent to about 15 percent urea, from about 1 percent to about 5 percent menthol, from about 0.5 percent to about 5 percent methyl salicylate, and from about 0.5 percent to about 5 percent camphor. All percentages expressed above are weight/volume, based upon the total volume of the formulation. In another aspect of the present invention, there is provided a method for the administration of leuprolide free base comprising percutaneously administering to a mammal in need of such treatment a formulation as described above.

DETAILED DESCRIPTION

Leuprolide, having the chemical structure shown above, has three ionizable sites: 1) the imidazolyl nitrogen atom of the histidyl amino acyl residue at position two, 2) the phenolic hydroxyl group of the tyrosyl amino acyl residue at position five, and 3) the terminal nitrogen atom of the guanidyl amino acyl residue at position eight. Thus leuprolide is capable of existing in both the free base form or in a salt form where one or more of the ionizable sites described above are convened to their corresponding acid addition or base addition salts. By the term "free base form" of leuprolide is meant the form in which none of the ionizable sites of the molecule have been convened into a salt form by reaction with an externally added acid or acids.

Leuprolide is typically synthesized by solid-phase peptide synthesis methods such as disclosed in U.S. Pat. No. 3,914,412 to Gendrich, et al., the teachings of which are incorporated herein by reference. Following such solid phase synthesis on an ion exchange resin, the peptide is usually displaced from the ion exchange resin as the trifluoroacetate salt and subsequently converted

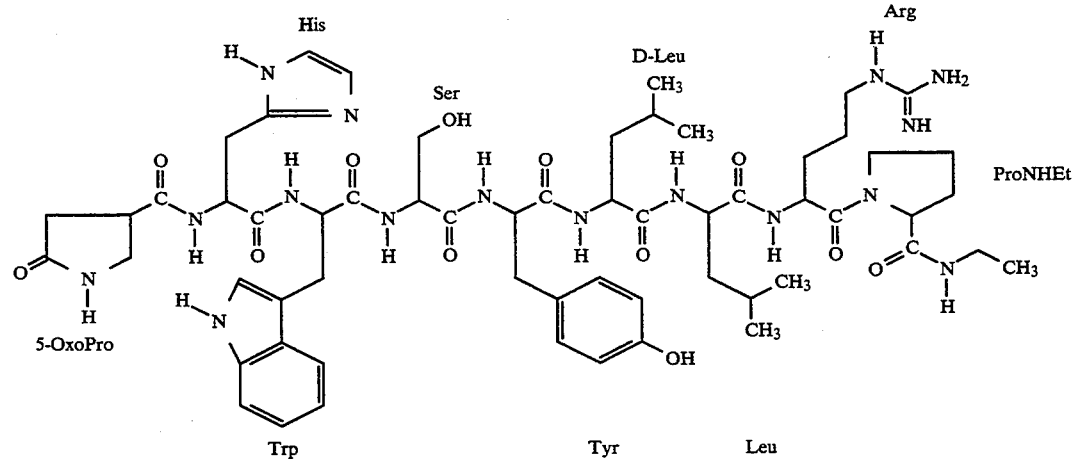

to the acetate salt form for use in pharmaceutical formulations for parenteral administration. The acetate salt has at least one mole of acetic acid per mol of leuprolide free base.

However, in the method of the present invention, the non-salt or free base form of leuprolide is employed. It has been found that the cutaneous permeability of the free base form of leuprolide is considerably greater than that of the conventionally-employed acetate salt form, particularly in formulations additionally containing a skin-penetration enhancing agent consisting of a mixture of menthol, camphor, methyl salicylate, and urea. As is shown by the data presented below, the effective transport of leuprolide base across human skin is accomplished when all four of the above-named ingredients make up the cutaneous membrane penetration enhancing component. The amount of leuprolide free base which transports through human skin is considerably decreased when only one, two, or three of the ingredients are present.

The formulations of the present invention may either be in the form of liquids or gels which are administered by means of skin patches, or in the form of ointments or creams which are administered topically. The compositions comprise from about 1 mg/ml to about 100 mg/ml, preferably from about 10 mg/ml to about 50 mg/ml, most preferably about 40 mg/ml of leuprolide free base, and from 3 percent to 30 percent, preferably from about 5 percent to about 20 percent of a cutaneous membrane penetration enhancing component. The cutaneous membrane penetration enhancing component consists essentially of from about 1 percent to about 15 percent, preferably from about 5 to about 12 percent, most preferably about 10 percent urea; from about 1 percent to about 5 percent, preferably from about 1 to about 3 percent, most preferably about 1 percent menthol; from about 0.5 percent to about 5 percent, preferably from about 1 percent to about 3 percent, most preferably about 2 percent methyl salicylate; and from about 0.5 percent to about 5 percent, preferably from about 0.5 percent to about 2 percent, most preferably about 1 percent, camphor. All percentages expressed above are weight/volume, based upon the total volume of the formulation.

The formulations of the present invention can take the form of ointments or creams which are administered topically by spreading on the skin or the form of gels or liquids which are administered by means of a skin patch. Methods of formulating ointment or cream and liquid or gel compositions are well known to those skilled in the as formulation arts. Typical ingredients for the non-therapeutic or "carrier" components of such formulations are listed, for example in "Dermatological Formulations," Brian W. Barry, Marcel Dekker, New York, 1983, pp. 325 ff., the teachings of which are incorporated herein by reference. Such carriers may include, depending upon whether the intended use of the composition is as an ointment or cream for direct application to the skin or as a liquid or gel formulation for administration by skin patch, non-therapeutic carrier components. Such components may serve as vehicles, either hydrophobic or water-miscible, structural matrix agents in creams, suspending or jelling agents, water-in-oil or oil-in-water emulsifiers, preservatives, buffers, humectants, antioxidants, and skin moisturizers.

Hydrophobic vehicles include liquid petrolatum, mineral oil, Neobee ® oil, white or yellow petrolatum, bees wax, microcrystalline wax and the like. Hydrophilic vehicles include water, alcohols such as ethanol, isopropyl alcohol, lauryl (i.e. dodecyl) alcohol, myristyl (i.e. tetradecyl) alcohol, cetyl (i.e. hexadecyl) alcohol, oleyl alcohol, benzyl alcohol, and p-phenoxyethyl alcohol, with ethanol or mixtures of ethanol and water being preferred in liquid compositions of the present invention.

Structural matrix agents or suspending or jelling agents in creams include petroleum jellies, colloidal silicon dioxide such as Cab-O-Sil ®, Aerosil ®, colloidal hydrated aluminum magnesium silicate, monmorillonite, polyethylene glycol, palmitic and stearic acids, and the like.

Water-in-oil or oil-in-water emulsifiers include myristyl and cetyl alcohols, lanolin and lanolin derivatives, palmitic, stearic, and oleic acids, bees wax, long chain sorbitan esters, and the like.

Humectants include glycerol, polyethylene glycols, 70% sorbitol solution, and the like.

Skin moisturizers include squalene, paraffin, microcrystalline wax, dimethylpolysiloxanes, sodium pyrrolidone carboxylate, sodium or potassium salts of lactic acid, and the like.

When administered as a cream or ointment, the compositions of the present invention are applied directly to the skin and rubbed into the skin. When administered by skin patch, the compositions of the present invention are placed, in the form of a liquid or gel, in the chamber of a typical skin patch device such as that described in "Transdermal Delivery of Drugs", Vol. 1., A. F. Kydonieus and B. Berner, Ed., CRC Press, Inc., Boca Raton, Fla. (1987).

To enable one skilled in the art to practice the present invention, the following illustrative examples are provided. These examples are not to be read as limiting the scope of the present invention as it is defined by the appended claims.

EXAMPLE 1

Preparation of Leuprolide Free Base

A solution of 1 gram of leuprolide acetate in 15 ml of methanol was loaded onto an anion exchange resin in the hydroxide ion form (Bio-Rad AG-1×2, 200–400 mesh, Bio-Rad Laboratories, 237-T Putnam Ave., Cambridge, Mass. 02139). The resin column had been prepared by passing a solution of 0.5M methanolic sodium hydroxide through a column of the resin in chloride ion form, as obtained from the manufacturer. The free base form of leuprolide was eluted from the column with methanol and the solvent removed by evaporation to yield leuprolide in the free base form. HPLC determination of the putiry of the eluted material indicated that it was 96.5% pure.

EXAMPLE 2

Preparation of Leuprolide Palmitate Salt

A methanol solution containing 0. 1 mmol of leuprolide free base (prepared according to the method of Example 1) and 0.1 mmol of palmitic acid (Sigma Chemical Co., P.O. Box 14508, St. Louis, Mo. 63178) was evaporated to dryness under s stream of dry nitrogen.

EXAMPLE 3

Preparation of Leuprolide Decanesulfonate Salt

A methanol solution containing 0.1 mmol of leuprolide free base (prepared according to the method of Example 1) and 0.1 mmol of palmitic acid (Sigma Chemical Co., P.O. Box 14508, St. Louis, Mo. 63178) was evaporated to dryness under a stream of dry nitrogen.

EXAMPLE 4

Gel/Liquid Formulation

The following components are thoroughly mixed for fifteen minutes or until a homogenous mixture is formed:
8 ml Ethanol
1 g Urea
200 μl Methyl salicylate
100 mg Menthol
100 mg Camphor
100 mg Leuprolide free base
200 mg Hydroxypropyl cellulose Following complete mixing of the above ingredients, water is added sufficient to make 10 ml and mixing is continued until a homogenous gel solution is formed.

EXAMPLE 5

Ointment/Cream Formulation

The following components are thoroughly mixed for fifteen minutes or until a homogenous mixture is formed:
5 ml Mineral oil
2 ml of Neobee M-5 oil
1 g Beeswax
200 μl of Methyl salicylate
1 g Urea
100 mg Menthol
200 mg Camphor
100 mg of Leuprolide free base Following complete mixing of the above ingredients, water is added sufficient to make 10 ml and mixing is continued until a homogenous gel solution is formed. The resulting ointment or cream is applied to the skin or intravaginally.

EXAMPLE 6

The following components are thoroughly mixed for fifteen minutes or until a homogenous mixture is formed:
3 ml Mineral oil
1 ml of Glycerin
50 mg of Promulgan D emulsifier
50 ml of Cetyl alcohol
100 mg Menthol
200 μl Methyl salicylate
100 mg Menthol
200 mg Camphor
100 mg of Leuprolide free base Following complete mixing of the above ingredients, water is added sufficient to make 10 ml and mixing is continued until a homogenous gel solution is formed. The resulting ointment or cream is applied to the skin or intravaginally.

Partitioning Studies

Partitioning studies of leuprolide free base and the acetate, palmitate, and decanesulfonate salts were conducted in Type I glass culture tubes fitted with poly(tetrafluroethylene)-lined caps. Octanol-saturated water was used to prepare solutions of leuprolide free base and the leuprolide salts at concentrations of 500 μg/ml. Ten ml of each solution and 10 ml of water-saturated octanol were placed in the glass tubes which were then tightly capped and shaken for 24 hours at 30° C. At the end of this time, the tubes were centrifuged at 2000 rpm for ten minutes. The water and octanol layers were separated and each analyzed for the concentrations of leuprolide or leuprolide salt. The octanol-water distribution coefficients, Kd, was calculated from the ratio of concentration in the non-aqueous phase and the aqueous phase. The results are presented in Table 1.

TABLE 1

| Octanol/Water Distribution Coefficients of Leuprolide Free Base and Several of Its Salts | |
|---|---|
| Compound | Octanol/Water Distribution Coefficient ($K_d$) |
| Leuprolide free base | 0.119 |
| Leuprolide acetate | 0.022 |
| Leuprolide palmitate | 0.940 |
| Leuprolide decanesulfonate | 15.353 |

As can be seen by the data presented in Table 1, the lipophilicity of leuprolide free base is roughly six times that of the acetate salt, as measured by the octanol/water distribution coefficient. The lipophilicities of the palmitate and decanesulfonate salts are correspondingly much higher, probably owing to the presence in these salts of the large hydrocarbon group associated with the palmitic and decanesulfonic acids employed in the salts. However, the penetration of leuprolide through human skin is not solely related to the lipophilicity of the form of leuprolide employed. If this were true, it would be expected that the palmitate and decanesulfonate salt forms of leuprolide should be readily transported through human skin, and would be the salts of choice for a percutaneous formulation containing leuprolide.

Formulations comprising the most preferred formulation containing 1% menthol, 1% camphor, 2% methyl salicylate, and 10% urea in a solvent system of 4/1 (v/v) ethanol/water containing 2% hydroxypropyl cellulose and a concentration of 40 mg/ml of leuprolide were tested for permeability through these human skin preparations. The results appear in Table 2.

TABLE 2

| Comparison of Lipophilicity and Permeability Through Human Skin Tissue of Leuprolide Free Base and Several of Its Salts | | |
|---|---|---|
| Compound | Octanol/Water Distribution Coefficient ($K_d$) (From Table 1) | Permeability × 1000 (cm/hr) Mean (Standard Dev.) |
| Leuprolide free base | 0.119 | 2.119 (0.338) |
| Leuprolide acetate | 0.022 | 0.220 (0.115) |
| Leuprolide palmitate | 0.940 | ND* |
| Leuprolide decanesulfonate | 15.353 | ND* |

*Not detectable

As can be seen by the data appearing in Table 1, even in formulations containing the optimum skin penetration enhancing component, no detectable leuprolide was transported across human skin when the leuprolide was in the palmitate or decanesulfonate salt forms.

In vitro Diffusion Studies

In vitro diffusion studies of leuprolide free base, leuprolide acetate, leuprolide palmitate, and leuprolide decanesulfonate were carded out using a Franz diffusion apparatus (Vanguard International, Inc., Neptune, N.J.) and a Bronaugh flow-through system. The Bronaugh system is described by R. Bronaugh, R. Stewart, and S. Morton, "Methods for in vitro Percutaneous Absorption Studies VII: Use of Excised Human Skin," *J. Pharm. Sci.*, 75:1094–1097 (1986). In each test, the area of exposed cutaneous tissue was 4.52 cm$^2$ in the Franz cells and 0.32 cm$^2$ in the Bronaugh system. The dose of formulation employed was 0.4 ml for the Franz apparatus and 0.13 ml for the Bronaugh flow-though system. The test solution was charged to the donor cell of the apparatus in each case, after which the donor cell was sealed with parafilm. A solution of 40% PEG 400/60% 0.1M HEPES buffer (N-2-hydroxyethylpiperazine-N'-2-ethanesulfonic acid buffer, Sigma Chemical Co., P.O. Box 14508, St. Louis, Mo. 63178) was placed in the receptor chamber of the apparatus. The apparatus was water-jacketed and maintained at a temperature of 37° C. throughout the tests.

Purity of materials and the possibility of chemical or enzymatic degradation of the materials was checked periodically during each experiment by analysis of samples withdrawn from the donor and receiver chambers. No metabolism of leuprolide was observed in any of the experiments during transport across the test cutaneous tissue membrane.

Aliquot samples were removed from the receptor chamber periodically for total experiment times of up to 36 hours after initial application of the test solution. Concentrations of leuprolide or leuprolide salt in each aliquot sample were measured by HPLC methods. The cumulative amount of leuprolide or its salt present in the aliquots, divided by the area of the cutaneous tissue were plotted as a function of time. The lag time (X-intercept) and flux (slope) of the data were determined by linear least squares regression analysis. The flux value was divided by the leuprolide or leuprolide salt concentration in the initial formulation to obtain permeability (P) values.

Tests with Human Cutaneous Tissue

Samples of human cutaneous tissue from the thigh area were obtained from the National Disease Research Interchange (Philadelphia, Pa.) and were dermatomed to a uniform thickness of 200–300μ and then frozen until use at $-70°$ C. Tissue samples were thawed and hydrated in saline solution overnight. The rehydrated tissue samples were mounted in the apparatus and preconditioned for 40 minutes prior to the application of the test formulation in each case. Each tissue sample, once mounted in the cell apparatus, was tested for barrier integrity by applying tritiated water to the tissue. Formulations were prepared which contained a 4/1 v/v vehicle of ethanol/water, 40 mg/ml of leuprolide free base, 2% Klucel ® and various ingredients making up the cutaneous penetration enhancing component as shown in Table 3.

TABLE 3

| | Permeability Through Human Skin Tissue of Leuprolide Free Base Compositions | | | | |
|---|---|---|---|---|---|
| Example | Percent Urea | Percent Menthol | Percent Camphor | Percent Methyl Salicylate | Permeability × 1000 (cm/hr) Mean (Standard Dev.) |
| 7 | 0 | 0 | 0 | 0 | 0.000 |
| 8 | 0 | 1 | 1 | 2 | 0.029 |
| 9 | 10 | 1 | 1 | 2 | 0.220 |
| 10 | 10 | 0 | 0 | 0 | 0.000 |

As can be seen from the data appearing in Table 3, compositions made up of leuprolide free base in a carrier, but lacking a skin penetration enhancing component (Example 7) showed no detectable permeability. Addition of menthol, camphor and methyl salicylate components (Example 8) improved the permeability, but not significantly. Only when all four ingredients (i.e. urea, menthol, camphor, and methyl salicylate) were employed in the cutaneous membrane penetration enhancing component of the formulations, was the pemeability significantly increased (Example 9). The effect appears to derive from the combination of ingredients, since use of urea alone (Example) or the other three components without the urea (Example) did not achieve such a high permeability.

The foregoing examples are provided to enable one skilled in the art to practice the present invention and are not to be read as limiting the scope of the present invention as it is defined by the appended claims.

We claim:

1. A composition for the percutaneous adiministration of leuprolide (Sequence ID No. 2) comprising
   a therapeutically effective amount of leuprolide free base;
   a cutaneous membrane penetration enhancing component comprising from about 3 percent to about 30 percent of the composition wherein said cutaneous membrane enhancing agent comprises
     from about 1 percent to about 15 percent urea,
     from 1 percent to about 5 percent menthol,
     from about 0.5 percent to about 5 percent methyl salicylate, and
     from about 0.5 percent to about 5 percent camphor; and
   a pharmaceutically acceptable carrier, all percentages in weight/volume, based upon the total volume of the composition.

2. A composition as defined by claim 1 wherein said leuprolide Seq. ID No. 2 free base is present in said composition in a concentration of between about 1 mg/ml and 100 mg/ml.

3. A composition as defined by claim 2 wherein said leuprolide Seq. ID No. 2 free base is present in said composition in a concentration of between about 10 mg/ml and 50 mg/ml.

4. A composition as defined by claim 1 wherein said composition is in the form of a liquid or gel.

5. A composition as defined by claim 1 wherein said composition is in the form of a cream or ointment.

6. A composition as defined by claim 1 wherein said cutaneous membrane penetration enhancing component consists essentially of
   from about 5 to about 12 percent urea;
   from about 1 to about 3 percent menthol;
   from about 1 percent to about 3 percent methyl salicylate; and
   from about 0.5 percent to about 2 percent camphor;
all percentages expressed as weight/volume, based upon the total volume of the formulation.

7. A composition as defined by claim 6 wherein said cutaneous membrane penetration enhancing component consists essentially of
   about 10 percent urea;
   about 1 percent menthol;
   about 1 percent methyl salicylate; and
   about 2 percent camphor;
all percentages expressed as weight/volume, based upon the total volume of the formulation.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="XAA at position 1 is a pyro- glutamyl residue"

-continued

```
( i x ) FEATURE:
        ( A ) NAME/KEY: Modified-site
        ( B ) LOCATION: 10
        ( D ) OTHER INFORMATION: /note="XAA at position 10 is a
              glycyl-amide residue"

( x i ) SEQUENCE DESCRIPTION: SEQ ID NO:1:

Xaa  His  Trp  Ser  Tyr  Gly  Leu  Arg  Pro  Xaa
    1              5                              10

( 2 ) INFORMATION FOR SEQ ID NO:2:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( A ) NAME/KEY: Modified-site
                ( B ) LOCATION: 1
                ( D ) OTHER INFORMATION: /note="XAA at position 1 is a
                      5-oxo-prolyl (i.e. pyro-glutamyl) residue"

( i x ) FEATURE:
                ( A ) NAME/KEY: Modified-site
                ( B ) LOCATION: 6
                ( D ) OTHER INFORMATION: /note="XAA at position 6 is a
                      D-leucyl residue"

( i x ) FEATURE:
                ( A ) NAME/KEY: Modified-site
                ( B ) LOCATION: 9
                ( D ) OTHER INFORMATION: /note="XAA at position 9 is a
                      prolyl-N- ethyl amide residue"

( x i ) SEQUENCE DESCRIPTION: SEQ ID NO:2:

Xaa  His  Trp  Ser  Tyr  Xaa  Leu  Arg  Xaa
    1              5
```